(12) United States Patent
Kralovec et al.

(10) Patent No.: US 11,649,473 B2
(45) Date of Patent: *May 16, 2023

(54) ENZYMATIC MODIFICATION OF OIL

(71) Applicant: DSM Nutritional Products AG, Kaiseraugst (CH)

(72) Inventors: Jaroslav A. Kralovec, Halifax (CA); Weijie Wang, Dartmouth (CA); James Colin Barrow, Torquay (AU)

(73) Assignee: DSM Nutritional Products AG, Kaiseraugst (CH)

(*) Notice: Subject to any disclaimer, the term of this patent is extended or adjusted under 35 U.S.C. 154(b) by 269 days.

This patent is subject to a terminal disclaimer.

(21) Appl. No.: 16/524,659

(22) Filed: Jul. 29, 2019

(65) Prior Publication Data
US 2019/0345524 A1     Nov. 14, 2019

Related U.S. Application Data

(60) Division of application No. 15/863,058, filed on Jan. 5, 2018, now Pat. No. 10,415,065, which is a continuation of application No. 13/789,811, filed on Mar. 8, 2013, now Pat. No. 9,885,068, which is a continuation of application No. 12/668,533, filed as
(Continued)

(51) Int. Cl.
| | | |
|---|---|---|
| *C12P 7/6409* | (2022.01) |
| *C12P 7/6418* | (2022.01) |
| *C12P 7/6445* | (2022.01) |
| *C12P 7/6472* | (2022.01) |

(Continued)

(52) U.S. Cl.
CPC .......... *C12P 7/6409* (2013.01); *C11C 1/045* (2013.01); *C12P 7/649* (2013.01); *C12P 7/6418* (2013.01); *C12P 7/6445* (2013.01); *C12P 7/6472* (2013.01); *Y02E 50/10* (2013.01)

(58) Field of Classification Search
CPC ..... C12P 7/6409; C12P 7/6418; C12P 7/6445; C12P 7/6472; C12P 7/649; C11C 1/045; Y02E 50/10
See application file for complete search history.

(56) References Cited

U.S. PATENT DOCUMENTS

| | | |
|---|---|---|
| 5,156,963 A | 10/1992 | Eigtved |
| 5,191,071 A | 3/1993 | Kirk et al. |
| | (Continued) | |

FOREIGN PATENT DOCUMENTS

| | | |
|---|---|---|
| EP | 1430782 A1 | 6/2004 |
| WO | WO9524459 | 9/1995 |
| | (Continued) | |

OTHER PUBLICATIONS

Ackman et al., Fish Oils, Bailey's Industrial Oil and Fat, 2005, 279-317.
(Continued)

*Primary Examiner* — Louise W Humphrey
*Assistant Examiner* — Anjali Ajit Hirani
(74) *Attorney, Agent, or Firm* — McBee Moore & Vanik IP, LLC

(57) ABSTRACT

The disclosed subject matter relates generally to a method for modifying oil, and specifically to a process for increasing the concentration of polyunsaturated fatty acid in an oil composition.

16 Claims, 1 Drawing Sheet

Specification includes a Sequence Listing.

Related U.S. Application Data application No. PCT/IB2008/003336 on Jul. 11, 2008, now Pat. No. 8,420,349.

(60) Provisional application No. 60/959,248, filed on Jul. 12, 2007.

(51) Int. Cl.
*C12P 7/649* (2022.01)
*C11C 1/04* (2006.01)

(56) References Cited

U.S. PATENT DOCUMENTS

| | | | |
|---|---|---|---|
| 5,945,318 | A | 8/1999 | Breivik et al. |
| 6,020,200 | A | 2/2000 | Enevold |
| 6,159,523 | A | 12/2000 | Cain et al. |
| 6,248,909 | B1 | 6/2001 | Akimoto et al. |
| 6,259,523 | B1 | 7/2001 | Welker |
| 6,518,049 | B1 | 2/2003 | Haraldsson et al. |
| 6,566,124 | B1 | 5/2003 | Trout et al. |
| 6,605,452 | B1 | 8/2003 | Basheer |
| 6,846,942 | B2 | 1/2005 | Rubin |
| 6,905,850 | B2 | 6/2005 | Irimescu et al. |
| 8,420,349 | B2 * | 4/2013 | Kralovec ............ C12P 7/6445 435/41 |
| 9,885,068 | B2 * | 2/2018 | Kralovec ............ C12P 7/6445 |
| 2004/0122093 | A1 | 6/2004 | Gandhi |
| 2005/0165101 | A1 | 7/2005 | Gandhi |
| 2006/0148047 | A1 | 7/2006 | Haraldsson et al. |
| 2007/0105204 | A1 | 5/2007 | Bao et al. |

FOREIGN PATENT DOCUMENTS

| | | |
|---|---|---|
| WO | WO9719601 | 6/1997 |
| WO | WO19970019601 A1 | 6/1997 |
| WO | WO0049117 | 8/2000 |
| WO | WO0073254 | 12/2000 |
| WO | WO0162906 A2 | 8/2001 |
| WO | WO0211746 A2 | 2/2002 |
| WO | WO2004043894 A1 | 5/2004 |
| WO | WO20080155410 A1 | 12/2008 |

OTHER PUBLICATIONS

Appel et al., Does Supplementation of Diet with 'Fish Oil' Reduce Blood Pressure?, Arch Intern Med, 1993, 1429-1438, 153(12).

Aravindan et al., Lipase applications in food industry, Indian Journal of Biotechnology, 2007, 141-158, 6.

Balaji et al., A facile and selective synthesis of B-Keto esters via zeolite catalysed transesterification, Journal Chemical Soc. Chem., 1996, 707-708, 1.

Bernstein et al., The Protein Data Bank: A Computer-based Archival File for Macromolecular Structures, J. Mol. Biol., 1977, 535-542, 112.

Bickerstaff et al., Immobilization of enzymes and cells, Humana Press, 1997, 1-12.

Bimbo et al., Technology of Production of Marine Oils, Marine Biogenic Lipids, Fats and Oils, 1989, 401-433.

Blossey et al., Concerning the use of polymer based photosensitizers, Tetrahedron Letter, 1974, 323-326, 4.

Buisman et al., Enzymatic esterifications of functionalized phenols for the synthesis of lipophilic antioxodants, Biotechnology Letters, 1998, 131-136, 20(2).

Chavan et al., Use of Solid Superacid (Sulphated SnO2) as Efficient Catalyst in Facile Transesterification of Ketoesters, Tetrahedron Letters, 1996, 233-236, 37(2).

Cvengros, Jan, Three-Stage Wiped-Film Molecular Evaporator: Design and Application, Chem. Eng. Technol., 1995, 49-58, 18.

Dyerberg et al., Bioavailability of n-3 Fatty Acid Formulations, n-3 Fatty Acids: Prevention and Treatment in Vascular Disease, 1995, 217-226, n/a.

El-Hamdy et al., Separation of Non-Polar Lipids by High Performance Liquid Chromatography on a Cyanopropyl Column, Journal of High Resolution Chromatography, 1993, 55-57, 16.

Fernandes et al., Hydrolysis and synthesis reactions catalysed by Thermomyces lanuginosa lipase in the AOT/Isooctane reversed micellar system, Journal of Molecular Catalysis B.: Enzymatic 30, 2004, 43-49, 30.

Freitas et al., Enzymatic hydrolysis of soybean oil using lipase from different sources to yield concentrated of polyunsaturated fatty acids, World J. Microbiol Biotechnol, 2007, 1725-1731, 23.

Haken, Studies in trans-esterification, J. Appl. Chem., 1963, 168-171, 13.

Haraldsson et al., The Preparation of triglycerides highly enriched with w-3 polyunsaturated fatty acids via lipase catalyzed interesterification, Tetrahedron Letters, 1989, 1671-74, 30(13).

Hoshino et al., Selective Hydrolysis of Fish Oil by Lipase to Concentrate n-3 Polyunsaturated Fatty Acids, Agricultural and Biological Chemistry, 1990, pp. 1459-1467, vol. 54, No. 6.

Moore et al., Production of Triglycerides Enriched in Long-Chain n-3 polyunsaturated Fatty Acids from Fish Oil, JAOCS, 1996, 1409-1414, 73(11).

Office Action for Application No. CL2008-002020 dated Aug. 1, 2013.

Singh et al., Thermomyces lanuginosus: properties of strains and their hemicellulases, FEMS Microbiology Reviews, 2003, 3-16, 27.

Torres et al., Lipase-catalyzed synthesis of designer acylglycerols rich in residues of eicosapentaenoic, docosahexaenoic, conjugated linoleic, and/or stearic acids, Eur. J. Lipid Sci. Technol., 2003, pp. 614-623, vol. 104.

Torres et al., Preparation of purified acylglycerols of eicosapentaenoic acid and docosahexaenoic acid and their re-esterification with conjugated linoleic acid, Enzyme and Microbial Technology, 2003, pp. 49-58, vol. 32.

Wanasundara et al., Lipase-Assisted Concentration of n-3 Polyunsaturated Fatty Acids in Acylglycerols from Marine Oils, JAOCS, 1998, 945-951, 75(8).

Willis et al., Biotechnological Strategies for the Modification of Food Lipids, Biotechnology and Genetic Engineering Reviews, 1999, 141-175, 16(1).

\* cited by examiner

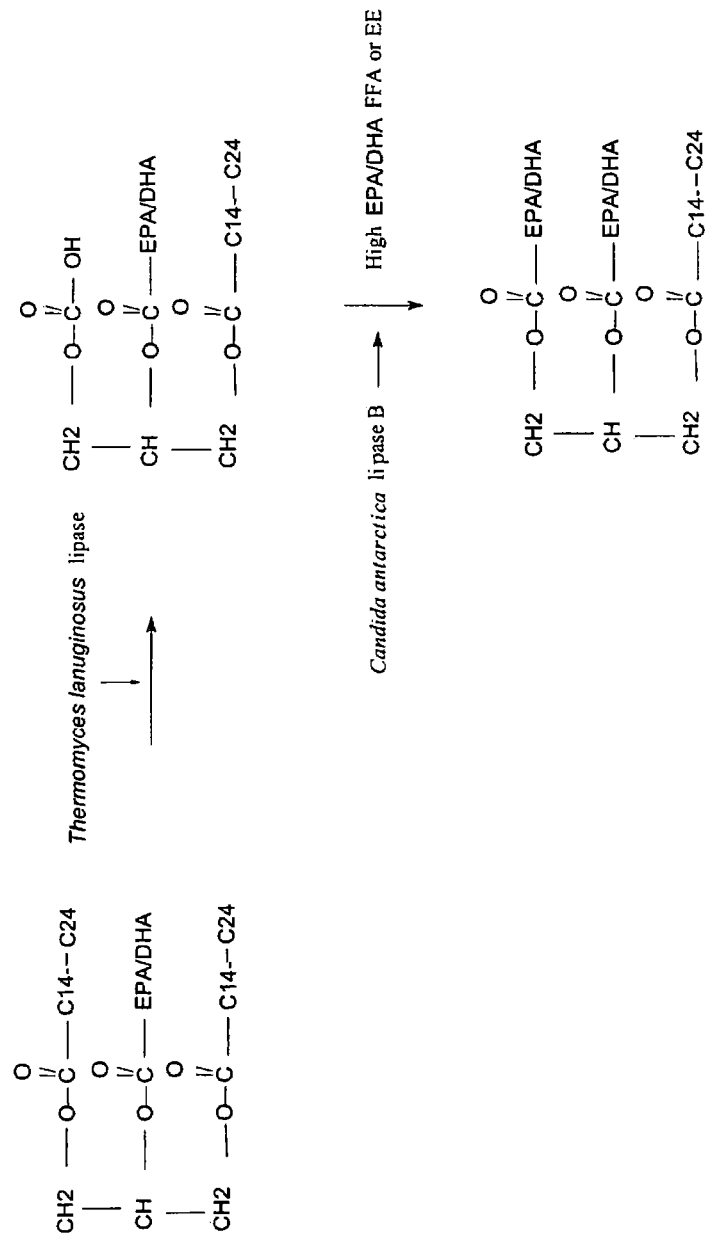

SEQUENCE LISTING

```
<160> NUMBER OF SEQ ID NOS: 1

<210> SEQ ID NO 1
<211> LENGTH: 291
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 1

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
                20                  25                  30

Asn Leu Phe Ala Gln Tyr Ser Ala Ala Tyr Cys Gly Lys Asn Asn
            35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220
```

```
Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
                260             265                 270

Asn Ile Pro Asp Ile Pro Ala His Leu Trp Tyr Phe Gly Leu Ile Gly
            275             280                 285

Thr Cys Leu
        290
```

ENZYMATIC MODIFICATION OF OIL

CROSS REFERENCE TO RELATED APPLICATIONS

The present application claims priority to U.S. Patent Application No. 60/959,248, filed Jul. 12, 2007, which application is incorporated herein fully by this reference.

FIELD

The disclosed subject matter relates generally to a method for modifying oil, and specifically to a process for increasing the concentration of polyunsaturated fatty acid in an oil composition.

BACKGROUND

Polyunsaturated fatty acids (PUFA) such as the omega-3 fatty acids are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits. See e.g., Dyrberg, et al., In: ω-3 Fatty Acids: Prevention and Treatment of Vascular Disease. Kristensen, et al., eds., Bi & Gi Publ., Verona-Springer-Verlag, London, pp. 217-26, 1995; O'Keefe and Harris, *Am. J. Cardiology* 2000, 85:1239-41; Radack et al., "The effects of low doses of omega-3 fatty acid supplementation on blood pressure in hypertensive subjects: a randomized controlled trial." *Arch. Intern. Med* 1991, 151:1173-1180. Indeed, the American Heart Association has also reported that omega-3 fatty acids can reduce cardiovascular and heart disease risk. Other benefits of PUFAs are those related to the prevention and/or treatment of inflammation, neurogenerative diseases, and cognitive development. See e.g., Sugano, Michihiro, "Balanced intake of polyunsaturated fatty acids for health benefits." *J. Oleo Sci.* 2001, 50(5):305-311. Diets rich in PUFA's like omega-3 fatty acids have also been shown to have beneficial effects for heart disease, cancer, arthritis, allergies, and other chronic diseases. (See e.g., The American Heart Association, Scientific Statement, "Fish Consumption, Fish Oil, Omega-3 Fatty Acids and Cardiovascular Disease," November 2002; Appel et al., "Does supplementation of diet with 'fish oil' reduce blood pressure? A meta-analysis of controlled clinical trials." *Arch. Intera. Med* 1993, 153(12):1429-1438; GISSI-Prevenzione Investigators. "Dietary supplementation with omega-3 polyunsaturated fatty acids and vitamin E after myocardial infarction: results of the GISSI-Prevenzione trial." *Lancet* 1999, 354:447-455.)

Polyunsaturated fatty acids, such as, for example omega-3 fatty acids, are often derived from marine oils, microbial, and/or algal oils. Such sources typically provide the PUFA in a triglyceride form where other undesired, fatty acids (e.g., saturated fatty acids) are present along side a desired PUFA in the triglyceride molecule. Thus, purifying and concentrating PUFA's in a triglyceride form is generally desired.

Several methods of producing PUFA concentrates from oils, such as marine, microbial, and/or algal oils, are known, for example, selective lipase hydrolysis, PUFA complexation using urea (or more sophisticated molecular guest-host frameworks involving metric control), and a physical removal of unwanted components by fractionation. U.S. Pat. No. 6,846,942 describes the separation of EPA from DHA by precipitating EPA magnesium salt. Fractionation involving molecular distillation is usually conducted on ethyl esters prepared from the starting triglycerides since they are more volatile than corresponding triglycerides. So this method requires the additional step of converting the triglycerides to ethyl esters. Since ethyl esters of PUFA are usually not as bioavailable as their triglyceride counterparts, the PUFA ethyl esters are typically re-esterified to the corresponding triglycerides.

A need exists to remove at least a fraction of the saturated free fatty acids and other undesirable components from a glyceride, such as for example, a triglyceride, and to concentrate the PUFA fraction on the glyceride. The compositions and methods disclosed herein meet these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to methods of modifying an oil composition, in particular marine, algal, and microbial oils. Processes for increasing the concentration of polyunsaturated fatty acids in an oil composition are also disclosed. Oils prepared by the disclosed methods are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURE

The accompanying FIGURE, which is incorporated in and constitutes a part of this specification, illustrates several aspects of the invention and, together with the description, serves to explain the principles of the invention.

FIG. 1 is a schematic of an exemplary process for the hydrolysis of a glyceride and subsequent esterification of a polyunsaturated fatty acid, in accordance with various aspects of the disclosed processes.

DETAILED DESCRIPTION

The materials, compounds, compositions, articles, and methods described herein may be understood more readily by reference to the following detailed description of specific aspects of the disclosed subject matter and the Examples included therein and to the FIGURE.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an unsaturated fatty acid" includes mixtures of two or more such unsaturated fatty acids, reference to "the enzyme" includes mixtures of two or more such enzymes, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value" and possible ranges between values are also disclosed, as appropriately understood by the skilled artisan. For example, if the value "10" is disclosed, then "lees than or equal to 10" as well as "greater than or equal to 10" is also disclosed. It is also understood that throughout the application, data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Reference will now be made in detail to specific aspects of the disclosed materials, compounds, compositions, articles, and methods, examples of which are illustrated in the accompanying Examples and FIGURE.

Methods

Disclosed herein is a method for removing at least a portion of a saturated and/or short chain fatty acid fraction of an oil composition comprising, for example, a glyceride, and esterifying at least a fraction of a PUFA to form a substituted triglyceride. In one aspect, the method can provide an oil having higher levels of a PUFA, such as, for example, EPA, DHA, or a combination thereof, than the starting oil composition. In a specific aspect, the various methods and aspects thereof can be used to replace a saturated and/or short chain fatty acid positioned on a glyceride, such as a diglyceride and/or a triglyceride, with a polyunsaturated fatty acid, such as an EPA, DHA, or a combination thereof.

The methods disclosed herein can be useful in, for example, hydrolyzing one or more saturated fatty acids from a starting glyceride using a lipase enzyme, and then removing the saturated fatty acids. The remaining glyceride (that is, the hydrolyzed glyceride) can then be esterified with one or more polyunsaturated fatty acids to provide a final glyceride product having a higher concentration in polyunsaturated fatty acids than the starting material. In one example, the one or more fatty acids hydrolyzed from a starting glyceride comprise at least one saturated or short chain fatty acid. In another example, the one or more polyunsaturated fatty acids comprise EPA, DHA, or a combination thereof. Depending upon the starting oil, glyceride, reaction conditions, and polyunsaturated fatty acid(s), the specific composition of a treated oil (e.g., glyceride) can be adjusted and/or tailored to have a target ratio of various polyunsaturated fatty acids. Such tailored compositions can be useful, for example, in providing glycerides that comprise high concentrations of DHA that exhibit greater oxidation resistance.

The disclosed enzymes in the disclosed processes can be expensive. Thus, ways to reuse the enzymes are of commercial significance. The enzymes described herein can be reused several times. For example, after the hydrolysis and/or esterification steps are complete, the solutions can be filtered off and the enzyme can be and reused. The enzyme can be washed optionally with a suitable solvent and/or water, which can be desirable depending upon the selection of the ester and alcohol used. For example, if the acid/ester and/or alcohol clog the enzyme, then it would be desirable to wash off the ester or alcohol in order to increase the efficiency of the enzyme. In one example, water can be used to wash the enzyme. For the purpose of storage, the product could be stored in the presence of food preservatives, e.g., sodium benzoate, potassium sorbate, etc.

The term "glyceride" is used to refer to any glyceride molecule disclosed herein, e.g., starting, hydrolyzed, and final glyceride molecules, as well as mono, di, and triglyceride molecules, unless the context specifically refers to one type of glycerides.

Starting Oil Composition

Oil that can be treated with the disclosed methods can be any suitable oil composition that comprises a glyceride. In one example, the starting oil composition can be a natural product, such as that derived from marine oil, microbial oil, algal oil, or a combination thereof. In another example, the starting oil composition can be a synthetic product, such as, for example a product derived from the esterification of a glycerol and a polyunsaturated fatty acid. In another example, the starting oil composition can be a combination of a natural product and a synthetic product.

In one specific example, the starting oil composition can be derived from marine oils, such as fish oil. Such oils typically contain mixtures of saturated and unsaturated fatty acids, esters, and glycerides thereof, but can be processed to result in a particular mixture of fatty acids (e.g., containing all saturated, all unsaturated, mixtures of both, or mixtures with fatty acids of a certain chain length or range of chain lengths). Any fish oil can be used in the disclosed compounds and methods. Examples of suitable fish oils include, but are not limited to, Atlantic fish oil, Pacific fish oil, Mediterranean fish oil, light pressed fish oil, alkaline treated fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmon oil, and shark oil, including mixtures and combinations thereof. Non-alkaline treated fish oil is also suitable. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed compositions and in the disclosed methods to prepare than. Further oils include, microbial oil, algal oil (e.g., oil from a dinoflagellate such as *Cryptheco-dinium cohnii*), fungal oil (e.g., oil from *Thraustochytrium*, *Schizochytrium*, or a mixture thereof), and/or plant oil, including mixtures and combinations thereof.

As noted, the starting oil composition comprises a glyceride, such as a diglyceride, a triglyceride, or combinations thereof. The glyceride in the starting oil (the starting glyceride) can comprise a plurality of fatty acids (saturated, unsaturated, and even short chain carboxylic acids). Vacant hydroxy groups can also be present in the glyceride starting oil. The particular fatty acids that can be removed using various aspects of the disclosed methods comprise one or more saturated and/or short chain fatty acids. Such a glyceride can also comprise one or more polyunsaturated fatty acids, such as an EPA and/or DHA.

As used herein, the term "fatty acid" is intended to represent a carboxylic acid with at least 10 carbon atoms. In one example, the fatty acid or the ester thereof can comprise at least 10, at least 12, at least 14, at least 16, at least 18, or at least 20 carbon atoms. In some specific examples, the fatty acid or the ester thereof can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In other examples, the fatty acid or the ester thereof can comprise a mixture of fatty acids or the esters thereof having a range of carbon atoms. For example, the fatty acid or the ester thereof can comprise from 10 to 40, from 12 to 38, from 14 to 36, from 16 to 34, from 18 to 32, or from 20 to 30 carbon atoms.

It is also understood that by the term "fatty acid," that the carboxyl group could be in either protonated or deprotonated form (i.e., meaning $RCO_2-$ as well as $RCO_2H$, where R is the hydrocarbyl chain). Thus, phrases like glyceride with a saturated fatty acid are understood to mean molecules where the carboxyl portion of the free saturated fatty acid is bonded to the glycerol molecule via an ester bond. This convention and nomenclature is typically used by those in the field.

The fatty acids or esters thereof can be saturated, unsaturated, or a mixture of saturated and unsaturated fatty acids. As used herein, the term "saturated" is intended to mean that the molecule or residue contains no carbon-carbon double or triple bounds. As used herein, the term "unsaturated" is intended to mean that the molecule or residue contains at least one carbon-carbon double or triple bond.

Hydrolysis

The hydrolysis step of the disclosed methods removes one or more saturated and/or short chain fatty acids, or esters thereof, from a starting glyceride, thus leaving a glyceride fraction (hydrolyzed glyceride) where glyceride molecules with unsubstituted alcohol groups and/or polyunsaturated fatty acid esters remain. By "hydrolyzed glyceride" is understood that the glyceride may be partially hydrolyzed or completely hydrolyzed. Also, both partially and completely hydrolyzed glycerides can be (and in many examples are) present. Thus, the term "hydrolyzed glyceride" is contemplated herein to include such partially and completely hydrolyzed glycerides. In another example, the hydrolysis step removes one or more saturated and/or short chain fatty acids, together with one or more mono or polyunsaturated fatty acids from the starting glyceride. In a further example, the hydrolysis step removes all or substantially all of any saturated and/or short chain fatty acids from the starting glyceride and does not remove a substantial amount of polyunsaturated fatty acids, if present, from the glyceride.

Examples of specific saturated fatty acids and esters thereof that can be removed with the hydrolysis step disclosed herein include, but are not limited to, capric acid (C10), lauric acid (C12), myristic acid (C14), palmitic acid (C16), margaric acid (C17), stearic acid (C18), arachidic acid (C20), bebenic acid (C22), lignoceric acid (C24), cerotic acid (C26), montanic acid (C28), and melissic acid (C30), including branched and substituted derivatives thereof. Shorter chain "fatty" acids like hexanoic (C6), hepanoic (C7), octanoic (C8), and nonanoic acid (C9) can also be removed by the disclosed methods.

The hydrolysis step comprises the use of a lipase enzyme in liquid form to hydrolyze at least a portion of the glyceride and provide a hydrolyzed glyceride fraction and a free saturated fatty acid fraction. In a specific example, the liquid lipase enzyme comprises *Thermomyces lanuginosus*, such as LIPOZYME™ TL100 (available from Novozymes A/S, Bagsvaerd, Denmark). This enzyme has the sequence MRSSLVLFFVSAWTALASPIRREVSQDLFNQFNL-FAQYSAAAYCGKNNDAPAGT NITCTGNACPEVEKA-DATFLYSFEDSGVGDVTGFLA-LDNTNKLIVLSFRGSRSIEN WIGNLNFDLKEINDICSGCRGHDGFTSSWRS-VADTLRQKVEDAVREHPDYRVVFT GHSLG-GALATVAGADLRGNGYDIDVFSYGAPRVGNRAFAE-FLTVQTGGTLYRIT HTNDIVPRLPPREFGYSHSSPEYWIKSGTLVPVTRN- DIVKIEGIDATGGNNQPNIPDI PAHLWYFGLIGTCL (SEQ ID NO:1). Enzymes with a sequence homology of at least 80, at least 85, at least 90, at least 95, at least 97, and at least 99% homology to SEQ ID NO:1 are also contemplated herein for use in the disclosed methods. In one example, the liquid lipase is a food-grade lipase. In another example, the liquid lipase is at least one of a kosher and/or halal-certified food grade liquid lipase.

The use of a liquid *Thermomyces lanuginosus* enzyme can allow for efficient hydrolysis and, thus, reduce the amount of enzyme needed to hydrolyze at least a portion of the fatty acid substituents from a glyceride. The amount of *Thermomyces lanuginosus* needed to achieve hydrolysis can be less than or significantly less than, for example, 50%, 25% or 10%, the amount of other lipase enzymes. Typically, the amount of *Thermomyces lanuginosus* used can be from about 0.01% to about 3.0%, from about 0.1% to about 2%, from about 0.2% to about 1.5%, from about 0.3% to about 1% of the total weight of the oil.

Prior to hydrolysis, the starting oil composition can optionally be washed with water and/or a pH buffer, such as a pH 10 buffer (e.g., a potassium carbonate, potassium borate, potassium hydroxide buffer, 0.05 M). An optional wash, if performed, can comprise one or more washes of the same of varying compositions and conditions. In one example, an oil composition is washed with 60° C. water. In another example, an oil composition is twice washed with 60° C. water. The quantity of wash solution (e.g., water, pH buffer, or other wash liquid), temperature, and duration of a wash can vary depending upon the starting oil composition and the desired outcome, such as, for example, purity, of a wash step. In a specific example, 100 grams of microbial oil is washed with two aliquots, 50 mL each, of 60° C. water. In another specific example, 100 grams of microbial oil is washed with a quantity of pH 10 buffer equivalent to approximately 20 weight % of the oil, followed by two water washes, each using a quantity of water equivalent to approximately 50 weight % of the oil. A pH buffer of buffer solution can comprise any suitable buffer and/or buffer solution for use with the specific oil composition. The specific pH of a buffer solution, if used, can vary and can range, in various examples, from about 7 to about 12. In one example, a pH 10 buffer comprises a potassium carbonate-potassium borate-potassium hydroxide buffer (0.05 M). After an optional washing step, the aqueous fraction of the wash can optionally be separated and removed from the oil composition.

The starting oil composition can then be contacted with an aqueous solution of a *Thermomyces lanuginosus* lipase. Contacting of the oil composition and the lipase solution can be performed either separate from, combined with, or subsequent to an optional washing step. In one example, an oil composition is twice washed with water, washed with a pH 10 buffer solution, and then contacted with an aqueous solution of the lipase enzyme. In another example, the aqueous solution of *Thermomyces lanuginosus* is a phosphate buffered solution of pH about 7.2 (0.01-0.1M).

The amount of liquid lipase used can vary. An aqueous solution of *Thermomyces lanuginosus* can be prepared by, for example, mixing a quantity of the lipase enzyme with water. The amount of lipase enzyme mixed with water, and thus, the concentration of a resulting lipase solution, can vary. In a specific example, about 0.20 grams of the lipase enzyme can be mixed with about 50 mL of water. The specific amount of liquid lipase enzyme can be greater than or less than the described ratios depending upon the specific materials and conditions and the methods disclosed herein are intended to include such examples. In other example, the amount of *Thermomyces lanuginosus* can be about 0.0001, 0.0002, 0.0005, 0.0007, 0.001, 0.0025, 0.005, 0.0075, 0.01, 0.025, 0.05, 0.075, 0.10, 0.25, 0.50, 0.75, 0.80, 0.85, 0.90, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% of the total weight of the oil, where any of the stated ranges can form an upper or lower endpoint of a range.

The conditions for hydrolysis of the starting glyceride can vary, depending upon the desired extent of hydrolysis and the specific reaction components, provided that at least a portion of the saturated fatty acid constituents on a glyceride are hydrolyzed. Thus, the phrase "at a time and temperature sufficient to hydrolyze at least a portion of the glyceride" can be selected by one of skill in the art, depending on the desired amount of hydrolysis and the desired final product, while monitoring the reaction by known analytical techniques. Thus, in general, longer reaction times, higher temperatures (within the limits of the lipase), and/or more amounts of lipase can be use for more complete hydrolysis.

After contacting the oil composition with the lipase enzyme, the resulting mixture can, in various examples, be sealed in an inert or substantially inert atmosphere, such as, for example, nitrogen or argon atmosphere. The resulting mixture can also be optionally agitated for a period of time sufficient to allow a desired amount of hydrolysis. In one example, an oil/lipase mixture is vigorously agitated for a period of from about 48 to about 72 hours at about 40° C. In various examples, the hydrolysis of one or more fatty acid substituents can take place at an elevated temperature. The precise elevated temperature can depend on the particular fatty acids present, the amount or concentration of the reagents, preference, and the like. Suitable temperatures at which the hydrolysis can occur include, but are not limited to, from about ambient to about 100° C., from about 35° C. to about 80° C., or from about 40° C. to about 50° C. In certain examples, the reaction time can be adjusted by varying the temperature. Thus, reaction times can vary from about 2 hours to about 72 hours or more, from about 24 hours to about 72 hours, from about 36 hours to about 72 hours, or from about 48 hours to 72 hours.

After hydrolysis, the hydrolyzed oil composition (comprising a glyceride fraction and free saturated fatty acid fraction) can optionally be washed with water one or more times. The aqueous portion of the mixture can then be separated from the non-aqueous portion, and the non-aqueous portion dried. Drying conditions can vary and the disclosed methods are not intended to be limited to any particular drying conditions. In one example, the non-aqueous portion is dried under vacuum at about 80° C.

In many examples, the hydrolysis step is conducted in water and in the absence of alcohol; thus the hydrolyzed product is a free saturated fatty acid and not a free saturated fatty ester.

In other examples, the lipase is not a lipase of *Candida rugosa* (also known as *Candida cylindracea*), *Geotrichum candidum*, *Mucor miehei*, *Penicillium roguefortii*, or *Pseudomonas fluorescens*. Such enzymes can remove selectively saturated fatty acids but they are not specific. As a result, when oils having high concentrations of polyunsaturated fatty acids are used these lipases will hydrolyze some of the polyunsaturated fatty acids from the glyceride molecule as well as the shorter and saturated fatty acids.

Separation

The hydrolyzed glyceride composition (i.e., the hydrolyzed glyceride fraction and free saturated fatty acid fraction) can then be separated by, for example, wipe film evaporators and/or short path distillation, to separate at least a portion of the free saturated fatty acid from the glyceride. Either a portion of, substantially all, or all of the free saturated fatty acid can, in various examples, be separated from the hydrolyzed glyceride fraction. It is preferred, but not necessary, that substantially all of the free saturated fatty acid fractions be separated from the hydrolyzed glyceride fraction prior to esterification to prevent re-esterification of undesirable components (e.g., the saturated fatty acids and short chain acids) to the glyceride. Any suitable separation technique can be used to fractionate the hydrolyzed glyceride and free saturated fatty acid fractions and the disclosed process is not intended to be limited to a particular fractionation technique or a specific set of fractionation conditions. One of skill in the art could readily select an appropriate fractionation technique to separate at least a portion of the hydrolyzed glyceride fraction from the saturated free fatty acid fraction in the hydrolyzed glyceride composition.

Since environmental pollutants such as pesticides and polychlorinated biphenyls (PCBs) are more volatile than glycerides of long chain fatty acids, molecular distillation will remove these compounds from the glyceride fraction whilst they will become concentrated in the distillate (saturated free fatty acid fraction). This is yet another advantage of the use of molecular distillation in the present process.

Winterization

At this stage, the use of a lipase to hydrolyze oil comprising a glyceride and then removing the saturated (and short chain) fatty acids, as disclosed herein, can be a substitute for a winterization process.

Winterization is a term used to describe the process of removing the high melting fractions (sterine or saturates) that solidify and cloud oils (e.g., algal oils and fish oils). The desired outcome of winterizing oil is to produce oil that remains clear and free of particulate. Typically, the winterization process involves cooling (e.g., to below minus 2° C.) in order to allow a crystal saturate molecule to form. Crystals then grow when several individual crystals come together and form a web of crystals that are significantly larger than the individual crystals. This is growth of the crystal has a direct impact on the ease of filtration of the oil and improperly formed crystals can lead to slow and ineffective filtration.

Once the oil has been held at temperature, the crystals are removed. This can be accomplished, for example, by centrifugation or by sending the mixture of oil and crystals to a filter press. The filtered oil is then collected in a holding tank and saturates are collected in the press. As noted, proper crystal formation is important, as this will directly affect the efficiency of the filtration. Large well-formed crystals will tend to stack one on top of the other and form a web that the clear oil can pass through easily. In contrast, smaller undeveloped crystals will tend to pack in very tightly, plugging off the pores in the filter cloth and reducing the flow almost immediately.

By the methods disclosed herein, such winterization processes that require cooling and crystal formation are not needed. Oils can be "winterized" by contacting them with an aqueous solution of a lipase (e.g., *Thermomyces lanuginosus*) and removing saturates by, for example, molecular distillation.

Esterification

After hydrolysis and separation, desirable polyunsaturated fatty acid components, for example, EPA and/or DHA, can be attached to the hydrolyzed and distilled glyceride using a lipase. In one example, the lipase enzyme can be immobilized in a food grade matrix. Each component of the disclosed immobilized enzymes is described below.

The terms "esterify" and "esterification" are meant to include the various specific types of reactions whereby a —C(O)O— bond is formed. It includes the conversion of a carboxylic acid to the corresponding ester by reacting the carboxylic acid with an alcohol to produce the ester (e.g., $RC(O)OH+R^1OH \rightarrow RC(O)OR^1+H_2O$). It also includes "transesterifaction," which is the conversion of one ester to another by reacting the ester with an alcohol to produce a different ester (e.g., $RCOOR^1+R^2OH \rightarrow RCOOR^2+R^1OH$). The term "interesterifcation" is also included herein and is the switching of ester moieties between two or more separate, independent esters. Interesterification between two esters is depicted in scheme 1A, where the $R^2$ and R groups are switched in the starting materials (i.e., $R^1C(O)OR^2$ and $R^3C(O)OR^4$). Scheme 1B depicts the interesterification between a carboxylic acid ($R^1C(O)OH$) and an ester ($R^3C(O)OR^4$), which produces a new carboxylic acid and ester. The term "intraesterify" is defined herein as the switching of ester moieties within the same molecule. Intraesterification is depicted in scheme 1C, where the $R^2$ and $R^3$ groups are switched in the triester. Scheme 1D depicts the intraesterification between a carboxylic acid group and an ester within the same molecule, where hydrogen of the carboxylic acid switches with $R^3$ of the ester group.

Scheme 1

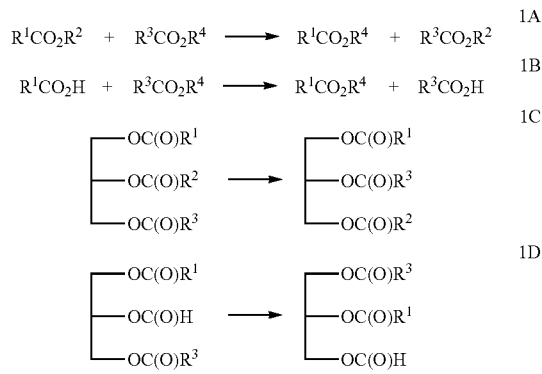

In the esterification step, one or more polyunsaturated fatty acids or esters thereof are coupled to a free hydroxyl group on the hydrolyzed glyceride via and ester bond. The polyunsaturated fatty acids or esters thereof suitable for the methods disclosed herein can comprise at least two unsaturated bond (i.e., a carbon-carbon double or triple bond). In one example, the unsaturated fatty acid or ester thereof can comprise at least 2, at least 3, at least 4, at least 5, at least 6, at least 7, at least 8, at least 9, or at least 10 carbon-carbon double bonds, triple bonds, or any combination thereof. In another example, the unsaturated fatty acid or ester thereof can comprise 1, 2, 3, 4, 5, 6, 7, 8, 9, or 10 unsaturated bonds, where any of the stated values can form an upper or lower endpoint when appropriate.

In some examples, the unsaturated fatty acids or esters thereof can comprise at least one pair of methylene interrupted unsaturated bonds. By "methylene interrupted unsaturated bond" is meant that one carbon-carbon double or triple bond is separated from another carbon-carbon double or triple bond by at least one methylene group (i.e., $CH_2$). Specific examples of unsaturated fatty acids or esters thereof that contain at least one pair of methylene interrupted unsaturated bonds include, but are not limited to, the n-1 family derived from 9, 12, 15-16:3; n-2 family derived from 9, 12, 15-17:3, 15:3, 17:3, 17:4, 20:4; n-3 family derived from 9, 12, 15-18:3, 15:2, 15:3, 15:4, 16:3, 16:4, 18:3 (α-linolenic), 18:4, 18:5, 20:2, 20:3, 20:4; 20:5 (EPA), 21:5, 22:3, 22:5 (DPA), 22:6 (DHA), 24:3, 24:4, 24:5, 24:6, 26:5, 26:6, 28:7, 30:5; n-4 family derived from 9, 12-16:2, 16:2, 16:3, 18:2, 18:3; n-5 family derived from 9, 12-17:2, 15:2, 17:2, 17:3, 19:2, 19:4, 20:3, 20:4, 21:4, 21:5; n-6 family derived from 9, 12-18:2, 15:2, 16:2, 18:2 (linoleic acid), 18:3 (γ-linolenic acid); 20:2, 20:3, 20:4 (arachidonic acid), 22:2, 22:3, 22:4 (adrenic acid), 22:5, 24:2, 24:4, 25:2, 26:2, 30:4; n-7 family derived from 9-16:1, 15:2, 16:2, 17:2, 18:2, 19:2; n-8 family derived from 9-17:1, 15:2, 16:2, 17:2, 18:2, 19:2; n-9 family derived from 9-18:1, 17:2, 18:2, 20:2, 20:3, 22:3, 22:4; n-11 family 19:2, and the n-12 family 20:2.

In the above paragraph, the compounds are identified by referring first to the "n-x family," where x is the position in the fatty acid where the first double bond begins. The numbering scheme begins at the terminal end of the fatty acid where, for example, the terminal $CH_3$ group is designated position 1. In this sense, the n-3 family would be an omega-3 fatty acid, as described herein. The next number identifies the total number of carbon atoms in the fatty acid. The third number, which is after the colon, designates the total number of double bonds in the fatty acid. So, for example, in the n-1 family, 16:3, refers to a 16 carbon long fatty acid with 3 double bonds, each separated by a methylene, wherein the first double bond begins at position 1, i.e., the terminal end of the fatty acid. In another example, in the n-6 family, 18:3, refers to an 18 carbon long fatty acid with 3 methylene separated double bonds beginning at position 6, i.e., the sixth carbon from the terminal end of the fatty acid, and so forth.

Some other examples are fatty acids or esters thereof that contain at least one pair of unsaturated bonds interrupted by more than one methylene group. Suitable examples of these acids and esters include, but are not limited to, those in the following Table 1:

TABLE 1

Examples of Polyene Acids

| Total number of carbon atoms in the fatty acid chain | Carbon number where double bond begins. ("c" denotes a cis double bond; "t" denotes a trans double bond) |
|---|---|
| 18 | 5, 9 |
| | 5, 11 |
| | 2t, 9, 12 |
| | 3t, 9, 12 |
| | 5t, 9, 12 |
| | 5, 9, 12 |
| | 5, 11, 14 |
| | 3t, 9, 12, 15 |
| | 5, 9, 12, 15 |
| 20 | 5, 11 |
| | 5, 13 |
| | 7, 11 |
| | 7, 13 |
| | 5, 11, 14 |
| | 7, 11, 14 |
| | 5, 11, 14, 17 |
| 22 | 5, 11 |
| | 5, 13 |
| | 7, 13 |
| | 7, 15 |
| | 7, 17 |
| | 9, 13 |
| | 9, 15 |

Still other examples of unsaturated fatty acids or esters thereof that are suitable for use in the methods disclosed herein are those that contain at least one conjugated unsaturated bond. By "conjugated unsaturated bond" is meant that at least one pair of carbon-carbon double and/or triple bonds are bonded together, without a methylene ($CH_2$) group between them (e.g., —CH═CH—CH═CH—). Specific examples of unsaturated fatty acids or esters thereof that contain conjugated unsaturated bonds include, but are not limited to, those in the following Table 2.

TABLE 2

Examples of Conjugated Polyene Acids

| Total number of carbon atoms in the fatty acid chain. | Carbon number where double bond begins. ("c" denotes a cis double bond; "t" denotes a trans double bond) |
|---|---|
| 10 | 2t, 4t, 6c |
| | 2c, 4t, 6t |
| | 3t, 5t, 7c |
| | 3c, 5t, 7t |
| 12 | 3, 5, 7, 9, 11 |
| 14 | 3, 5, 7, 9, 11 |
| 18 | 10t, 12t |
| | 8c, 10t, 12c (jacaric) |
| | 8t, 10t, 12c (calendic) |
| | 8t, 10t, 12t |
| | 9t, 11t, 13c (catalpic) |
| | 9c, 11t, 13t (α-eleostearic) |
| | 9c, 11t, 13c (punicic) |
| | 9t, 11t, 13t (β-eleostearic) |
| | 9c, 11t, 13t, 15c (α-parinaric) |
| | 9t, 11t, 13t, 15t (β-parinaric) |

Omega-3 fatty acids and esters thereof are also useful in the methods described herein. Omega-3 fatty acids are unsaturated fatty acids that are particularly useful in the compounds and methods disclosed herein. Omega-3 fatty acids not only exhibit proven effects on lowering serum triglyceride levels, but they have strong connection to diabetes. For instance, docosahexaenoic acid (DHA) also has a strong insulin permeability enhancement effect, and it is viewed as a potential absorption enhancer for intestinal delivery of insulin (Onuki et al., *Int. J. Pharm.* 198:147-56, 2000). DHA intake prevents certain biochemical processes that originate from insulin deficiency (Ovide-Bordeaux and Grynberg, *Am. J. Physiol. Regul. Integr. Comp. Physiol.* 286:R519-27, 2003) and both DHA and EPA (eicosapentaenoic acid) significantly increase fasting insulin levels (Mori et al., *Am. J. Clin. Nutr.* 71:1085-94, 2000).

An omega-3 fatty acid is an unsaturated fatty acid that contains as its terminus $CH_3$—$CH_2$—CH═CH—. Specific examples of omega-3 fatty acids and esters thereof that are suitable for use herein include, but are not limited to, linolenic acid (18:3ω3), octadecatetraenoic acid (18:4ω3), eicosapentaenoic acid (20:5ω3) (EPA), docosahexaenoic acid (22:6ω3) (DHA), docosapentaenoic acid (22:6ω3) (DPA), derivatives thereof and mixtures thereof.

In still other examples, unsaturated fatty acids and esters thereof can be derived from a compound comprising the following formula:

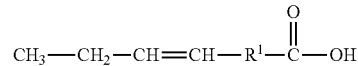

wherein $R^1$ is a $C_3$-$C_{40}$ alkyl or alkenyl group comprising at least one double bond. The term "alkane" or "alkyl" as used herein is a saturated hydrocarbon group. The term "alkene" or "alkenyl" as used herein is a hydrocarbon group of at least 2 carbon atoms with a structural formula containing at least one carbon-carbon double bond. Asymmetric structures such as (AB)C=C(CD) are intended to include both the E and Z isomers (cis and trans). This may be presumed in structural formulae herein wherein an asymmetric alkene is present, or it may be explicitly indicated by the bond symbol C=C. In a further example, $R^1$ can be a $C_5$-$C_{38}$, $C_6$-$C_{36}$, $C_8$-$C_{34}$, $C_{10}$-$C_{32}$, $C_{12}$-$C_{30}$, $C_{14}$-$C_{28}$, $C_{16}$-$C_{26}$, or $C_{18}$-$C_{24}$ alkenyl group. In yet another example, the alkenyl group of $R^1$ can have from 2 to 6, from 3 to 6, from 4 to 6, or from 5 to 6 double bonds. Still further, the alkenyl group of $R^1$ can have from 1, 2, 3, 4, 5, or 6 double bonds, where any of the stated values can form an upper or lower endpoint when appropriate.

Some specific examples of unsaturated fatty acids and esters thereof that can be used in the methods disclosed herein include, but are not limited to, linoleic acid, linolenic acid, γ-linolenic acid, arachidonic acid, mead acid, stearidonic acid, α-elostearic acid, eleostearic acid, pinolenic acid, docosadienic acid, docosatetraenoic acid, docosapentaenoic acid, docosahexaenoic acid, octadecadienoic acid, octadecatrienoic acid, eicosatetraenoic acid, eicosapentaenoic, or any combination thereof. In one example, the unsaturated fatty acid ester can be derived from linolenic acid (18:3ω03), octadecatetraenoic acid (18:4ω3), eicosapentaenoic acid (20:5ω3) (EPA), eicosatetraenoic acid (20:4ω3), henicosapentaenoic acid (21:5ω3), docosahexaenoic acid (22:6ω3) (DHA), docosapentacnoic acid (22:5ω3) (DPA), including derivatives and mixtures thereof.

Additional examples of suitable unsaturated fatty acid and esters thereof that are suitable in the methods include, but are not limited to, allenic and acetylenic acids, such as C14: 2, 4, 5; C18: 5, 6 (laballenic); 5, 6, 16 (lamenallenic); C18: 6a (tarinic); 9a; 9a, 11t (ximenynic); 9a, 11a; 9a, 11a, 13c (bolekic); 9a, 11a, 13a, 15e, 8a, 10t (pyrulic) 9c, 12a (crepenynic); 9c, 12a, 14c (dehydrocrepenynic acid); 6a, 9c, 12c; 6a, 9c, 12c, 15c, 8a, 11c, 14c and corresponding Δ17e derivatives, 8-OH derivatives, and Δ17e, 8-OH derivatives.

The enzymes useful herein for esterification are any naturally-occurring or synthetic enzymes that can be used to esterify a carboxylic acid or transesterify an ester. That is, any lipase can be used to esterify glycerol. Suitable enzymes can be derived from a microorganism. Examples of microorganisms that can produce enzymes useful herein include, but are not limited to, *Burkholderia* sp., *Candida antarctica* B, *Candida rugosa*, *Candida cylindracea*, *Pseudomonas* sp., *Candida antarctica* A, Porcine pancreas, *Humicola* sp., *Humicola lanuginose*, *Mucor miehei*, *Rhizopus javan.*, *Pseudomonas fluorescens*, *Pseudomonas cepacia*, *Candida cylindracae*, *Aspergillus niger*, *Rhizopus oryzae*, *Mucor jaanicus*, *Mucor javanicus*, *Rhizopus* sp., *Rhizopus japonicus*, *Rhizomucor miehei*, *Rhizopus niveus*, or *Penicillium camembertii* (also *Rhizopus delemar*, *Pseudonomas, aeruginosa*). Examples of using such enzymes to esterify glycerides are disclosed in U.S. Pat. Nos. 6,259,523, 6,020,020, which are incorporated by reference herein in their entireties.

In one example, the enzyme is produced from *Candida antarctica*. NOVOZYME™ CALB L is a lipase (lipase B) from *Candida antarctica* produced by submerged fermentation of a genetically modified *Aspergillus oryzae* microorganism. NOVOZYME™ CALB L is a highly versatile bio-catalyst with activity towards a great variety of different substrates. The enzyme is used in particular as a powerful enantioselective catalyst in the synthesis of optically active alcohols, amines, and carboxylic acids. *Candida antarctica* lipase B is known to effectively convert ethyl esters or free fatty acids to triglycerides. This enzyme is a protein with 317 amino acid residues and molecular weight of 33,008 Daltons. The amino acids are assembled into 14 α-helixes and 9 β-sheets. The sequence and secondary structure of *Candida antarctica* lipase B are provided in SEQ ID NO:1.

It is also contemplated that derivatives of enzymes produced from microorganisms can be immobilized and used in the methods described herein. It is understood that the structure of many enzymes, as disclosed herein, are known and can be found, for example, at Genbank, and are herein incorporated by reference.

As all microbial lipases, CALB belongs to α/β hydrolases, the fold of which comprises of eight-stranded β-sheets sandwiched between two layers of amphiplilic α-helices. The mechanism of ester hydrolysis of these enzymes generally involves binding to the ester substrate, formation of the first tetrahedral intermediate by nucleophilic attack of the catalytic serine with the oxyanion stabilized by two or three H-bonds, the so-called oxyanion hole. The ester bond is cleaved and the acylated enzyme is hydrolyzed in the final step. The nucleophilic attack by the catalytic serine is mediated by the catalytic histidine and aspartic or glutamic acid residue. In certain examples, the longest fatty acid chain that completely binds inside the binding pocket of CALB is C13; thus, the scisille fatty acid binding site of this enzyme is relatively short (13.5 Å). The binding site of CALB is relatively short and has a small hydrophobic area located at the wall of the binding funnel. Structure of CALB has been published in the Protein Data Bank (The Protein Data Bank: a computer-based archival file for macromolecular structures. Bernstein et al., *J. Mol. Biol.* 112:525-542, 1977). It is also understood that the disclosed enzymes can be defined by their own conserved catalytic cores that are understood in the art and are herein disclosed.

The amount of polyunsaturated fatty acid or ester and hydrolyzed glyceride can vary depending upon the fatty acid desired, the starting glyceride, and degree of hydrolysis. In one example, a stoichiometric amount of polyunsaturated fatty acid or ester relative to number of hydroxyl groups present on the hydrolyzed glyceride can be used. For example, if the hydrolyzed glyceride contains two free alcohols, then two molar equivalents of polyunsaturated fatty acid or ester can be esterified with one molar equivalent of the glyceride. An excess of hydrolyzed glyceride can be used to achieve maximum esterification as well as decrease the overall reaction time. In one example, the molar ratio of polyunsaturated fatty acid or ester to hydrolyzed glyceride can be from about 1:1 to about 10:1, from about 1:1 to about 9:1, from about 1:1 to about 8:1, from about 1:1 to about 7:1, from about 1:1 to about 6:1, from about 1:1 to about 5:1, from about 1:1 to about 4:1, or from about 1:1 to about 3:1.

The amount of the enzyme (enzyme and matrix together) can also vary as well. In one example, the enzyme is from 0.1% to 20% by weight of total weight of polyunsaturated fatty acid/ester and hydrolyzed glyceride. In other examples, the enzyme is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20% by weight of the total reaction, where any value can form an endpoint of a range.

The polyunsaturated fatty acid/ester, the hydrolyzed glyceride, and the enzyme can be admixed with one another in any order. Depending upon the selection of the polyunsaturated fatty acid/ester, it can be desirable to conduct the esterification while the reaction mixture is stirred. For example, a solution of ester and alcohol can be added to one another under stirring followed by the addition of the enzyme. Also the reaction mixture could be forced to pass through the bed of immobilized enzyme and this could be executed either in continuous or batch (single or recycled) process.

In certain examples, the esterification reaction can take place at an elevated temperature. The precise elevated temperature can depend on the particular polyunsaturated fatty acid/ester being used, the particular hydrolyzed glyceride being used, the amount or concentration of the reagents, preference, and the like. Suitable temperatures at which the esterification reactions can occur include, but are not limited to, from about 50° C. to about 100° C., from about 70° C. to about 90° C., from about 80° C. to about 90° C., or about 85° C. In another example, the esterification temperature can be from about 60° C. to about 70° C., or about 65° C. By varying the temperature it is possible to reduce reaction times depending upon the concentration of starting materials. Thus, reaction times can vary from 2 hours to 72 hours, 10 hours to 48, 10 hours to 36, 10 hours to 24 hours, 15 hours to 24 hours, 20 hours to 24 hours, or 22 hours.

In some examples, the method involves esterifying eicosapentaenoic acid 20:5ω3 (EPA), docosahexaenoic acid 22:6ω3 (DEA), docosapentaenoic acid 22:5ω3 (DPA), or any mixture thereof with hydrolyzed glyceride, wherein the acid and the alcohol are present in a molar ratio of from about 2:1 to about 5:1, wherein the reaction is stirred in the presence of the enzyme at a temperature of from about 60° C. to about 90° C. for about 2 hours to about 24 hours, wherein the enzyme comprises an enzyme derived from *Candida antarctica* immobilized in a food grade matrix comprising a copolymer of divinylbenzene and styrene.

In another example, the method involves transesterifying an ethyl ester of eicosapentaenoic acid 20:5ω3 (EPA), docosahexaenoic acid 22:6ω3 (DHA), docosapentaenoic acid 22:5ω3 (DPA), or any mixture thereof with hydrolyzed glyceride, wherein the ester and the alcohol are present in a molar ratio of from about 2:1 to about 5:1, wherein the reaction is stirred in the presence of the immobilized enzyme at a temperature of from about 55° C. to about 90° C. for about 20 hours to about 24 hours, wherein the immobilized enzyme comprises an enzyme derived from *Candida antarctica* immobilized in a food grade matrix comprising a copolymer of divinylbenzene and styrene.

The esterification step can be performed under anhydrous conditions. For example, the esterification step can be performed neat, where the hydrolyzed glyceride is combined with the second lipase in the absence of solvent. Alternatively, the esterification step can be performed in the presence of an anhydrous, organic solvent.

Enzymes

As discussed herein, numerous variants and strain derivatives of the disclosed enzymes, such as LIPOZYME™ TL100 used for the hydrolysis step and CALB (SEQ ID NO:1) used for the esterification step, are known and herein contemplated. Protein variants and derivatives are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues but can occur at a number of different locations at once; insertions usually will be on the order of from about 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 3 and 4 and are referred to as conservative substitutions.

TABLE 3

Amino Acid Abbreviations

| Amino Acid | Abbreviations |
|---|---|
| Alanine | Ala (A) |
| alloisoleucine | AIle |
| Arginine | Arg (R) |
| Asparagines | Asn (N) |
| aspartic acid | Asp (D) |
| Cysteine | Cys (C) |
| Glutamic acid | Glu (E) |
| Glutamine | Gln (Q) |
| glycine | Gly (G) |
| histidine | His (H) |
| isolelucine | Ile (I) |
| leucine | Leu (L) |
| lysine | Lys (K) |
| phenylalanine | Phe (F) |
| proline | Pro (P) |
| pyroglutamic acid | Glu |
| serine | Ser (S) |
| threonine | Thr (T) |
| tyrosine | Tyr(Y) |
| tryptophan | Trp (W) |
| valine | Val (V) |

TABLE 4

Amino Acid Substitutions
Original Residue Exemplary Conservative Substitutions, others are known in the art.

Ala ↔ ser
Arg ↔ lys or gln
Asn ↔ gln or his
Asp ↔ glu
Cys ↔ ser
Gln ↔ asn or lys
Glu ↔ asp TABLE 4-continued Amino Acid Substitutions
Original Residue Exemplary Conservative
Substitutions, others are known in the art.

Gly ↔ pro
His ↔ asn or gln
Ile ↔ leu or val
Leu ↔ ile or val
Lys ↔ arg or gln;
Met ↔ Leu or ile
Phemet ↔ leu or tyr
Ser ↔ thr
Thr ↔ ser
Trp ↔ tyr
Tyr ↔ trp or phe
Val ↔ ile or leu Substantial changes in function or immunological identity are made by selecting substitutions that are less conservative than those in Table 3, i.e., selecting residues that differ more significantly in their effect on maintaining: (a) the structure of the polypeptide backbone in the area of the substitution, for example as a sheet or helical conformation; (b) the charge or hydrophobicity of the molecule at the target site; or (c) the bulk of the side chain. The substitutions that are generally expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or replacing one polar residue for another. The substitutions include combinations such as, for example, Gly, Ala; Val, Ile, Leu; Asp, Glu; Asn, Gln; Ser, Thr, Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the ω-amino groups of lysine, arginine, and histidine side chains (T. E. Creighton, Proteins: Structure and Molecular Properties, W. H. Freeman & Co., San Francisco pp 79-86 (1983)), acetylation of the N-terminal amine and, in some instances, amidation of the C-terminal carboxyl.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular strain from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 3 and Table 4. The opposite stereoisomers of naturally occurring peptides are disclosed, as well as the stereoisomers of peptide analogs. These amino acids can readily be incorporated into polypeptide chains by charging tRNA molecules with the amino acid of choice and engineering genetic constructs that utilize, for example, amber codons to insert the analog amino acid into a peptide chain in a site specific way (Thorson et al., *Meth. Mol. Biol.* 77:43-73, 1991; Zoller, *Curr. Opinion Biotechnol.* 3:348-354, 1992; Ibba, *Biotechnol. Gen. Eng. Rev.* 13:197-216, 1995; Cahill et al., *TIBS* 14(10):400-403, 1989; Benner, *TIB Tech* 12:158-163, 1994; Ibba and Hennecke, *Bio/technology* 12:678-682, 1994, all of which are herein incorporated by reference at least for their material related to amino acid analogs).

Molecules can be produced that resemble peptides, but which are not connected via a natural peptide linkage. For example, linkages for amino acids or amino acid analogs can include, but are not limited to, $CH_2NH$—, —$CH_2S$—, —$CH_2$—$CH_2$—, —CH=CH— (cis and trans), —$COCH_2$—, —$CH(OH)CH_2$—, and —$CHH_2SO$— (These and others can be found in Spatola, in Chemistry and Biochemistry of Amino Acids, Peptides, and Proteins, B. Weinstein, eds., Marcel Dekker, New York, p. 267, 1983; Spatola, Vega Data (March 1983), Vol. 1, Issue 3, Peptide Backbone Modifications (general review); Morley, *Trends Pharm. Sci.* 463-468, 1980; Hudson et al., *Int. J. Pept. Prot. Res.* 14:177-185, 1979 (—$CH_2NH$—, $CH_2CH_2$—); Spatola et al., *Life Sci.* 38:1243-1249, 1986 (—$CH_2$—S); Hann, *J. Chem. Soc Perkin Trans.* 1307-314, 1982 (—CH=CH—, cis and trans); Almquist et al., *J. Med Chem.* 23:1392-1398, 1980 (—$COCH_2$—); Jennings-White et al., *Tetrahedron Lett.* 23:2533, 1982 (—$COCH_2$—); Szelke et al., European App. No. EP 45665 CA (1982): 97:39405 (1982) (—CH(OH)$CH_2$—); Holladay et al., *Tetrahedron. Lett.* 24:4401-4404, 1983 (—C(OH)$CH_2$—); and Hruby, *Life Sci.* 31:189-199, 1982 (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, *Ann. Rev. Biochem.* 61:387, 1992 that is incorporated herein by reference).

Sequence Similarities

It is understood that one way to define the variants and derivatives of the disclosed proteins herein is through defining the variants and derivatives in terms of homology/identity to specific known sequences. For example, SEQ ID NO:1 sets forth a particular sequence of a lipase. Specifically disclosed are variants of these and other proteins herein disclosed which have at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 homology to the stated sequence. Those of skill in the art readily understand how to determine the homology of two proteins. For example, the homology can be calculated after aligning the two sequences so that the homology is at its highest level.

It is understood that as discussed herein the use of the terms "homology" and "identity" mean the same thing as similarity. Thus, for example, if the use of the word homology is used between two non-natural sequences, it is understood that this is not necessarily indicating an evolutionary relationship between these two sequences but, rather, is looking at the similarity or relatedness between their sequences. Many of the methods for determining homology between two evolutionarily related molecules are routinely applied to any two or more nucleic acids or proteins for the purpose of measuring sequence similarity, regardless of whether they are evolutionarily related or not.

One way of calculating homology can be performed by published algorithms. Optimal alignment of sequences for comparison can be conducted by the local homology algorithm of Smith and Waterman, *Adv. Appl. Math.* 2:482, 1981, by the homology alignment algorithm of Needleman and Wunsch, *J. Mol. Biol.* 48:443, 1970, by the search for similarity method of Pearson and Lipman, *Proc. Natl. Acad Sci. U.S.A.* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, *Science* 244:48-52, 1989, Jaeger et al., *Proc. Natl. Acad Sci. U.S.A.* 86:7706-7710, 1989, Jaeger et al., *Methods Enzymol.* 183:281-306, 1989, which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity and be disclosed herein.

Another way of calculating homology can be performed by published algorithms. Optimal alignment of sequences for comparison can be conducted by the local homology algorithm of Smith and Waterman, *Adv. Appl. Math.* 2:482, 1981, by the homology alignment algorithm of Needleman and Wunsch, *J. Mol. Biol.* 48:443, 1970, by the search for similarity method of Pearson and Lipman, *Proc. Natl. Acad Sci. U.S.A.* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages). It is understood that the description of conservative mutations and homology can be combined together in any combination, such as aspects that have at least 70% homology to a particular sequence wherein the variants are conservative mutations.

Hybridization/Selective Hybridization

It is also understood that the enzymes disclosed herein, such as SEQ ID NO:1, can be classified by the ability of the nucleic acids encoding them to hybridize with other nucleic acids. The term "hybridization" typically means a sequence driven interaction between at least two nucleic acid molecules, such as a primer or a probe and a gene. The phrase "sequence driven interaction" means an interaction that occurs between two nucleotides or nucleotide analogs or nucleotide derivatives in a nucleotide specific manner. For example, G interacting with C or A interacting with T are sequence driven interactions. Typically, sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some examples selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12 to about 25° C. below the $T_m$ (the melting temperature at which half of the molecules dissociate from their hybridization partners), followed by washing at a combination of temperature and salt concentration chosen so that the washing temperature is about 5° C. to about 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154: 367, 1987, which is herein incorporated by reference for material at least related to hybridization of nucleic acids). A preferable stringent hybridization condition for a DNA: DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in, for example, 10, or 100, or 1000 fold excess. This type of assay can be performed at under conditions where both the limiting and non-limiting primer are, for example, 10 fold, or 100 fold, or 1000 fold below their $k_d$, or where only one of the nucleic acid molecules is 10 fold, or 100 fold, or 1000 fold, or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation; for example, if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example, if 80% hybridization was required and as long as hybridization occurs within the required parameters in any one of these methods it is considered disclosed herein.

It is understood that those of skill in the art understand that if a composition or method meets any one of these criteria for determining hybridization either collectively or to singly it is a composition or method that is disclosed herein.

Food Grade

The enzymes used in the disclosed processes can be "food grade." By food grade is meant is any material that is cleared by the U.S. Food and Drug Administration as a Secondary Direct Food Additive under 21 C.F.R. § 173. Sections 5-165 of 21 C.F.R. § 173 provide representative examples of materials useful as the food grade material as well as permissible amounts of impurities to be considered a food grade material useful herein. For example, the food grade material can comprise less than 10%, less than 8%, less than 6%, less than 4%, or less than 2% by weight non-polymerizable impurities.

Immobilized Enzymes

In certain examples, the enzymes can be immobilized onto a food grade matrix, which can comprise an acrylate-acrylamide resin (173.5), a polyacrylamide resin (173.10), an ion exchange resin (173.25), a perfluorinated ion exchange membrane (173.21), an ion exchange membrane (173.20), a molecular sieve resin (173.40), polymaleic acid or the sodium salt thereof (173.45), polyvinylpolypyrrolidone (173.50), polyvinylpyrrolidone (173.55), dimethylamine-epichlorohydrin copolymer (173.60), chloromethylated aminated styrene-divinylbenzene resin (173.70), sodium polyacrylate (173.73), or sorbitan monooleate (173.75), where the number in parenthesis is the federal registration section number that provides information with respect to the requirements of the material to be a secondary direct food additive. In other examples, the food grade matrix can comprise a copolymer of divinylbenzene. For example, the food grade matrix can comprise a copolymer of (1) divinylbenzene and (2) acrylic acid, methacrylic acid, methyl acrylate, methyl methacrylate, ethyl vinyl benzene, or styrene. Title 21 C.F.R. § 173.65 provides the requirements for the use of divinylbenzene copolymers as a secondary direct food additive. For example, the divinylbenzene copolymer must have at least 79 weight percent divinylbenzene and no more than 4 weight percent non-polymerizable impurities. Examples of divinylbenzene copolymers useful herein as food grade matrices include, but are not limited to, AMBERLITE™ XAD16HP, AMBERLITE™ FPX600, AMBERLITE™ FPX66, and DUOLITE™ A7, all of which are manufactured by Rohm and Haas (Philadelphia, Pa.). AMBERLITE™ XAD16HP and FPX600 are crosslinked, macroporous polystyrene/divinylbenzene copolymers. In one specific example, the enzyme is *Candida antarctica* lipase B and the food grade matrix is AMBERLITE™ XAD16HP.

The production of immobilized enzymes generally involves admixing the enzyme with the material used to produce the food grade matrix in a solvent such as, for example, water. In one example, a surfactant is not used in the preparation of the immobilized enzyme. Immobilization parameters such as pH, temperature, duration of immobilization, etc. will vary depending upon the selection of the enzyme and food grade matrix material. After immobilization is complete, the solution is drained and the resultant enzyme-matrix can be washed with water or other suitable solvents. The selection of solvents for the preparation of the immobilized enzyme should be a material that is compatible with human consumption. Thus, water is a preferred solvent. After the enzyme has been immobilized, the enzyme-matrix can be dried under reduced pressure and/or at elevated temperature, or using other gas or liquid media ($N_2$, Ar, oil etc.).

The enzyme can be immobilized on the matrix via covalent or no-covalent (e.g., electrostatic, ionic, hydrogen bonding, adsorption, entrapment, encapsulation, etc.) attachments or bonds depending upon the selection of the enzyme and food grade matrix, as well as immobilization conditions. Not wishing to be bound by theory, it is believed that immobilization of the enzyme on the matrix renders the enzyme significantly more stable due to the fixation of the enzyme conformation. If possible, the enzyme should not leach from the matrix, which will increase the efficiency of the esterification, transesterification, or interesterification/intraesterification process as well as prolong the life of the immobilized enzyme for future use. It is also desirable that the enzymes attached to the surface of the matrix be such that the enzymes expose their catalytic center.

The amount of enzyme immobilized on the matrix can vary and will depend upon the enzyme and matrix selected and the end-use of the immobilized enzyme. In one example, the amount of enzyme immobilized in the matrix is from about 7.5 to about 35 KLU (kilo lipase units) per gram of matrix based on the difference in the enzyme concentration in the solution used to interact with the matrix, as measured at 280 nm. In other examples, the amount of enzyme immobilized on the matrix can be about 7.5, 8, 9, 10, 11, 12, 13, 14, 15, 16, 17, 18, 19, 20, 21, 22, 23, 24, 25, 26, 27, 28, 29, 30, 31, 32, 33, 34, or 35 KLU/g matrix, where any value can form an end-point of a range. In another example, the amount of enzyme immobilized in the matrix is from about 28 to about 32 KLU/g matrix.

The immobilized matrix can be prepared by methods disclosed herein. In certain examples, the disclosed immobilized matrix can be prepared on a laboratory, pilot, or manufacturing scale. For example, the system shown in FIGS. 1 and 3 can be used for the preparation of pilot and manufacturing scale immobilized enzymes. Further, more than one bed of enzyme can be used. That is, one can used processes where more than one fixed enzyme bed reactor containing the disclosed immobilized enzymes are connected in serial or parallel. The number of reactors will depend on the desired amounts of production and starting materials. Various geometries of enzyme reactors can also be used.

Compositions

Compositions prepared by the disclosed methods are also contemplated. By the methods disclosed herein, concentrated oils with triglycerides containing higher proportions of polyunsaturated fatty acid esters than the starting glycerides can be produced. For example, the disclosed compositions can comprise triglycerides with higher DHA or balanced DHA/EPA contents than the starting triglycerides. Further, "designer" glycerides having specifically designed, and often non-naturally occurring ratios of polyunsaturated fatty acid ester can be prepared. Still further, using the disclosed methods to produce triglycerides of fatty acids, which are often more bioavailable than corresponding ethyl esters, can result in triglycerides that have better color and lower levels of trans-isomers, CDs, polymers, and side products. The disclosed methods can also result in triglycerides that have better sensory properties. Such oils can be incorporated into food products, nutraceuticals, pharmaceutical formulations, and microcapsules, which are additional advantages of the disclosed methods and compositions.

Compositions disclosed herein can be algal oils and fish oils as outlined in Table 5.

TABLE 5

Exemplary oils according to the disclosed processes

| Parameters | Oil after the disclosed hydrolysis and esterification | |
|---|---|---|
| | Algae oil | High DHA fish oil (D40) |
| Omega-3 PUFA | 50-80% | >40% |
| Saturated fatty acid | 18-45% | 22-25% |
| C18:1 fatty acid | 1-6% | 6-15% |
| C16:1 fatty acid and | 0-7% | 5-10% |
| EPA/DHA ratio | <1/40 | <1/15 |
| TG content | 60-80% | 60-80% |

In some specific examples, disclosed are oils that comprise greater than or equal to about 50%, 55%, 60%, 65%, 70%, 75%, or 80% omega-3 poly unsaturated fatty acids by weight of the total composition, where any of the stated values can form an upper or lower endpoint of a range. For example, the disclosed oils can comprise from about 50% to about 80%, from about 60% to about 80%, from about 70% to about 80%, from about 50% to about 70%, from about 50% to about 60%, or from about 60% to about 70% omega-3 polyunsaturated fatty acids by weight of the total composition. In other examples, disclosed are oils that comprise greater than or equal to about 40%, 45%, 50%, 55%, 60%, 65%, 70%, 75%, or 80% DHA by weight of the total composition, where any of the stated values can form an upper or lower endpoint of a range. For example, the disclosed oils can comprise from about 40% to about 90%, from about 50% to about 90%, from about 60% to about 90%, from about 70% to about 90%, from about 80% to about 90%, from about 40% to about 80%, from about 40% to about 70%, from about 40% to about 60%, from about 40% to about 50%, from about 50% to about 80%, or from about 60% to about 70% DHA by weight of the total composition.

In further examples, disclosed are oils that comprise greater than or equal to about 18%, 20%, 22%, 24%, 26%, 28%, 30%, 32%, 34%, 36%, 38%, 40%, 42%, 44%, or 45% saturates by weight of the total composition, where any of the stated values can form an upper or lower endpoint of a range. For example the oil can comprise from about 18% to about 45%, from about 20% to about 44%, from about 22% to about 40%, from about 24% to about 38%, from about 26% to about 36%, from about 28% to about 34%, from about 30% to about 45%, from about 20% to about 30%, or from about 22% to about 26% saturates by weight of the total composition.

In still further examples, disclosed are oils that can comprise about 1%, 2%, 3%, 4%, 5%, 6%, 7%, 8%, 9%, 10%, 11%, 12%, 13%, 14%, or 15% C18:1 fatty acid by weight of the total composition, where any of the stated values can form an upper or lower endpoint of a range. For example, the disclosed oil can comprise from about 1% to about 15, from about 1% to about 6%, from about 6% to about 15%, from about 3% to about 10%, or from about 5% to about 8% C18:1 fatty acid by weight of the total composition.

In still further examples, disclosed are oils that can comprise about 0%, 1%, 2%, 3%, 4%, 5%, 6%, 7%, 8%, 9%, or 10% C16:1 fatty acid, where any of the stated values can form an upper or lower endpoint of a range. For example, the disclosed oil can comprise from about 0% to about 10%, from 0% to about 7%, from about 5% to about 10%, from about 1% to about 5%, from about 3% to about 10%, or from about 5% to about 8% C16:1 fatty acid by weight of the total composition.

The amount of EPA and DHA present in the disclosed oils can be described in terms of the wt. % ratio of EPA to DHA. For example, the wt. % ratio of EPA to DHA in the disclosed oils can be about <1/40 (i.e., less than about 1 wt. % EPA to about 40 wt. % DHA, based on the total weight of the composition). Other wt. % ratios of EPA to DHA that can be present in the disclosed compositions include, but are not limited to, about <1:30, about <1:20, and about <1:15.

The disclosed oils can also have a high TG (triglyceride) content. For example, the oil can comprise greater than or equal to about 60%, 65%, 70%, 75%, or 80% TG by weight of the total composition, where any of the stated values can form an upper or lower endpoint of a range. For example, the disclosed oil can comprise from about 60% to about 80%, from about 70% to about 80%, from about 65% to about 75% TG by weight of the total compositions.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention that are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

In a first example, a 100 gram sample of a microbial oil was twice washed with 50 mL aliquots of approximately 60° C. water, after which the aqueous phase was removed. An enzyme solution was then prepared by mixing 0.20 g of Thermomyces lanuginosus lipase (LIPOZYME™ TL100 liquid, available from Novozymes A/S, Bagsvaerd, Denmark) with 50 mL of water. The washed oil was then added to the prepared enzyme solution and the resulting mixture vigorously stirred under a nitrogen atmosphere at 40° C. for 48 hours. The mixture was then allowed to settle and the aqueous phase separated. The oil was then washed two more times with 50 mL aliquots of water and then dried at 80° C.-90° C. under vacuum. The resulting free fatty acid (FFA) and glyceride fractions of the oil were then separated using short-path distillation. The fatty acid profile of each fraction and of the starting oil is detailed in Table 6, below.

TABLE 6

| | Fatty acid compositions (area %) | | |
|---|---|---|---|
| | | Oil | |
| Fatty acid | Microbial oil (a) | Glyceride fraction | FFA fraction |
| 14:0 | 8.3 | 5.9 | 14.5 |
| 14:1 | 0.1 | 0.1 | 0.2 |
| 15:0 | 0.4 | 0.2 | 0.7 |
| 16:0 | 21.3 | 13.5 | 44.7 |
| 16:1 | 0.2 | 0.2 | 0.5 |
| 16:2 | 0.2 | 0.2 | 0.3 |
| 17:1 | 0.1 | 0.1 | 0.0 |
| 16:4 | 0.1 | 0.1 | 0.2 |
| 18:0 | 0.5 | 0.3 | 1.2 |
| 18:1 | 1.0 | 0.8 | 2.5 |
| 18:2 | 0.3 | 0.4 | 0.8 |
| 18:3 | 0.3 | 0.4 | 0.4 |
| 18:4 | 0.3 | 0.3 | 0.3 |
| 20:0 | 0.1 | 0.1 | 0.3 |
| 20:3 | 0.6 | 0.6 | 0.5 |
| 20:4 | 3.3 | 3.4 | 2.9 |
| 20:5 | 1.3 | 1.2 | 2.0 |
| 22:0 | 0.0 | 0.1 | 0.3 |
| 22:5 | 17.4 | 20.0 | 8.2 |
| 22:6 | 43.8 | 51.1 | 19.1 |

Example 2

In a second example, a series of microbial oil samples were hydrolyzed to remove at least a fraction of a fatty acid. For each sample, a 100 gram oil sample was twice washed with a quantity of a pH 10 buffer solution equivalent to approximately 20% of the oil weight, after which the oil was twice washed with a quantity of water equivalent to approximately 50% of the oil weight and/or a quantity of Thermomyces lanuginosus lipase equivalent to approximately 1% of the oil weight. Table 7, below, illustrates the yield values of the glyceride fractions and the fatty acid (FA) compositions.

TABLE 7

| | Glyceride yields (wt %) and comparison of FA compositions (area %) | | | | | |
|---|---|---|---|---|---|---|
| | | | | Fatty acid composition (%) | | |
| Sample | Process | Yield (%) | Saturate | Mono | PUFA | DPA/DHA |
| Microbial Oil (a) | Starting oil | — | 30.6 | 1.5 | 67.1 | 17.0/43.8 |
| Glyceride sample A | Oil washed by water before hydrolysis, 0.20% enzymatic | 81.4 | 20.1 | 1.2 | 77.5 | 19.7/51.1 |
| Glyceride sample B | Oil washed by buffer and then by water before hydrolysis, 0.20% enzymatic | 72.6 | 19.6 | 1.1 | 78.3 | 19.9/52.2 |
| Glyceride sample E | Oil washed by water before hydrolysis, 1% enzymatic | 62.0 | 19.7 | 1.5 | 78.3 | 19.4/53.2 |

TABLE 7-continued

Glyceride yields (wt %) and comparison of FA compositions (area %)

| Sample | Process | Yield (%) | Satu-rate | Mono | PUFA | DPA/DHA |
|---|---|---|---|---|---|---|
| Glyceride sample D | Oil washed by buffer and then by water before hydrolysis, 1% enzymatic | 54.7 | 18.0 | 0.6 | 81.4 | 20.6/55.2 |

Example 3

In a third example, the hydrolyzed compositions prepared in Example 2, above, were esterified with at least one of three different high EPA or DHA concentrated free fatty acids (FFA): FFA20/48, FFA24/54 and FFA5/16 (EPA/DHA), respectively. For each composition, approximately 20 grams of glyceride oil was mixed with 5.71 grams of a concentrated FFA, after which approximately 0.52 grams of immobilized *Candida antarctica* lipase B was added. Each reaction was performed at 75-80° C. for 22 hours with gentle agitation under vacuum (1-10 mTorr). The resulting mixtures were then cooled to 25° C. and filtered to remove the immobilized enzyme. Lipid class results and fatty acid compositions are shown below in Tables 8.1 and 8.2, respectively.

TABLE 8.1

Lipid class and PUFA contents of algae oil and glyceride fraction after hydrolysis and the TG products after re-esterification

| Sample | PUFA (area %) | Lipid class (area %) | | | |
|---|---|---|---|---|---|
| | | FFA | TG | DG | MG |
| Microbial Oil (a) | 67.1 | 0.0 | 100 | 0.0 | 0.0 |
| Glyceride fraction after hydrolysis and distillation | 78.3 | 0.0 | 67.0 | 33.0 | 0.0 |
| After glyceride/FFA20/48 enzymatic re-esterification | 79.9 | 1.2 | 98.5 | 0.3 | 0.0 |
| After glyceride/FFA24/54 enzymatic re-esterification | 82.0 | 1.0 | 99.0 | 0.0 | 0.0 |
| After glyceride/FFA55/16 enzymatic re-esterification | 82.1 | 1.0 | 99.0 | 0.0 | 0.0 |

As detailed in Table 8.1, above, hydrolysis and re-esterification of the glyceride fraction of microbial oil resulted in the substantial formation of triglyceride comprising at least about 80 area % polyunsaturated fatty acids.

TABLE 8.2

Fatty acid profiles (area %) of the glyceride fraction and the TG products after re-esterification

| | Oil | | | |
|---|---|---|---|---|
| Fatty acid | Glyceride fraction | Glyceride/FFA20/48 enzymatic re-esterification | Glyceride/FFA24/54 enzymatic re-esterification | Glyceride/FFA55/16 enzymatic re-esterification |
| 14:0 | 5.9 | 4.6 | 4.8 | 4.2 |
| 14:1 | 0.1 | 0.1 | 0.0 | 0.0 |
| 15:0 | 0.2 | 0.2 | 0.3 | 0.2 |
| 15:1 | 0.0 | 0.0 | 0.0 | 0.0 |
| 16:0 | 13.0 | 10.3 | 10.6 | 10.2 |
| 16:1 | 0.2 | 0.3 | 0.2 | 0.3 |
| 16:2 | 0.2 | 0.1 | 0.2 | 0.0 |
| 17:1 | 0.1 | 0.1 | 0.0 | 0.0 |
| 16:4 | 0.1 | 0.1 | 0.0 | 0.0 |
| 18:0 | 0.3 | 0.4 | 0.3 | 0.6 |
| 18:1 | 0.7 | 0.8 | 1.2 | 1.5 |
| 18:2 | 0.3 | 0.3 | 0.3 | 0.3 |
| 18:3 | 0.3 | 0.3 | 0.4 | 0.0 |
| 18:4 | 0.3 | 0.3 | 0.6 | 0.4 |
| 20:0 | 0.1 | 0.1 | 0.0 | 0.0 |
| 20:1 | 0.0 | 0.4 | 0.0 | 0.4 |
| 20:3 | 0.6 | 0.5 | 0.6 | 0.3 |
| 20:4 | 3.1 | 2.9 | 4.1 | 3.0 |
| 20:5 | 1.0 | 5.2 | 12.9 | 7.0 |
| 22:0 | 0.1 | 0.3 | 0.0 | 0.0 |
| 22:1 | 0.0 | 1.2 | 0.0 | 0.0 |
| 21:5 | 0.0 | 0.5 | 1.0 | 0.4 |
| 22:4 | 0.0 | 0.2 | 0.4 | 0.0 |
| 22:5 | 20.2 | 17.8 | 16.8 | 16.5 |
| 22:6 | 52.2 | 51.7 | 44.9 | 54.2 |
| 24:1 | 0.0 | 0.6 | 0.0 | 0.0 |
| % Identified | 99.0 | 99.4 | 99.4 | 99.5 |

Example 4

In a fourth example, a second microbial oil comprising a higher concentration of saturated fatty acids was hydrolyzed according to the process described in Example 1, except that the concentration of *Thermomyces lanuginosus* lipase was approximately 0.3% of the oil weight. After hydrolysis and removal of the free fatty acid fraction by molecule distillation, the glyceride fraction (44% yield) was used to react with FFA55/16 under the same condition as in Example 3. The fatty acid compositions and lipid class of the starting oil, the glyceride and FFA fractions of hydrolyzed oil and re-esterified products are shown below in Tables 9.1 and 9.2, respectively.

TABLE 9.1

Fatty acid profiles (area %)

| | Oil | | | |
|---|---|---|---|---|
| Fatty acid | Microbial oil (b) | Glyceride fraction | FFA fraction | Glyceride/FFA55/16 enzymatic re-esterification |
| 14:0 | 19.4 | 14.8 | 23.1 | 11.6 |
| 15:0 | 1.2 | 0.8 | 1.5 | 0.7 |
| 15:1 | 0.0 | 0.0 | 0.0 | 0.0 |
| 16:0 | 35.4 | 21.7 | 46.6 | 17.3 |
| 16:1 | 8.6 | 7.6 | 9.4 | 6.1 |
| 17:0 | 0.2 | 0.0 | 0.3 | 0.1 |
| 16:4 | 0.0 | 0.0 | 0.0 | 0.0 |
| 18:0 | 1.0 | 0.7 | 1.3 | 0.7 |
| 18:1 | 5.9 | 5.4 | 6.4 | 5.0 |
| 18:3 | 0.0 | 0.0 | 0.0 | 0.1 |
| 18:4 | 0.0 | 0.0 | 0.0 | 0.5 |
| 20:3 | 0.0 | 0.0 | 0.0 | 0.2 |
| 20:4 | 0.9 | 1.4 | 0.0 | 2.5 |

TABLE 9.1-continued

Fatty acid profiles (area %)

| | Oil | | | |
|---|---|---|---|---|
| Fatty acid | Microbial oil (b) | Glyceride fraction | FFA fraction | Glyceride/FFA55/16 enzymatic re-esterification |
| 20:5 | 0.6 | 0.7 | 0.5 | 12.4 |
| 21:5 | 0.0 | 0.0 | 0.0 | 0.5 |
| 22:2 | 0.0 | 0.0 | 0.0 | 0.5 |
| 22:5 | 4.6 | 8.1 | 1.9 | 7.3 |
| 22:6 | 22.0 | 38.8 | 8.7 | 34.5 |
| % Identified | 99.7 | 100 | 99.7 | 100 |
| % Saturate | 57.2 | 38.0 | 72.8 | 30.4 |
| % Monounsaturate | 14.5 | 13.0 | 15.8 | 11.1 |
| % Polyunsaturate | 28.0 | 49.0 | 11.1 | 58.5 |

TABLE 9.2

Lipid class

| | Lipid class (area %) | | | |
|---|---|---|---|---|
| Sample # | FFA | TG | DG | MG |
| Microbial oil (b) | 0.0 | 100 | 0.0 | 0.0 |
| Glyceride fraction | 0.0 | 57.0 | 43.0 | 0.0 |
| FFA fraction | 96.0 | 0.0 | 1.0 | 4.0 |
| TG product | 3.5 | 91.2 | 5.3 | 0.0 |

Example 5

In a fifth example, a refined tuna oil was hydrolyzed according to the process described in Example 1 except the *Thermomyces lanuginosus* lipase was used at 0.25% of the oil weight. After hydrolysis and removal of the FFA by molecule distillation (60% yield), the glyceride fraction was used to react with FFA05/55 under the same conditions as in Example 3. Comparison of the fatty acid composition of starting oil, the glyceride fraction of hydrolyzed oil and re-esterified product is shown below in Tables 10.1 and 10.2.

TABLE 10.1

Fatty acid profiles (area %) of oil samples

| | Oil | | | | |
|---|---|---|---|---|---|
| Fatty acid | Tuna oil | Glyceride fraction | Glyceride/FFA20/48 enzymatic re-esterification | Glyceride/FFA24/54 enzymatic re-esterification | Glyceride/FFA55/16 enzymatic re-esterification |
| 14:0 | 3.2 | 2.7 | 2.0 | 2.1 | 2.3 |
| 14:1 | 0.1 | 0.0 | 0.1 | 0.0 | 0.1 |
| 15:0 | 0.9 | 0.8 | 0.6 | 0.6 | 0.5 |
| 15:1 | 0.1 | .0 | 0.0 | 0.1 | 0.0 |
| 16:0 | 19.3 | 15.2 | 11.8 | 10.1 | 10.8 |
| 16:1 | 4.9 | 4.3 | 2.9 | 2.8 | 3.1 |
| 16:2 | 0.8 | 0.7 | 0.5 | 0.4 | 0.5 |
| 17:0 | 1.5 | 1.3 | 1.0 | 0.7 | 1.0 |
| 17:1 | 0.6 | 0.7 | 0.5 | 0.3 | 0.4 |
| 16:4 | 0.2 | 0.0 | 0.0 | 0.1 | 0.2 |
| 18:0 | 5.5 | 3.9 | 3.1 | 2.6 | 2.6 |
| 18:1 | 16.0 | 11.7 | 9.1 | 9.0 | 9.3 |
| 18:2 | 1.5 | 1.5 | 0.9 | 1.1 | 1.2 |
| 18:3 | 0.5 | 0.3 | 0.3 | 0.5 | 0.8 |
| 19:0 | 0.2 | 0.0 | 0.1 | 0.1 | 0.1 |
| 18:4 | 0.9 | 1.1 | 0.9 | 1.1 | 1.5 |
| 20:0 | 0.3 | 0.3 | 0.3 | 0.3 | 0.2 |
| 20:1 | 1.8 | 1.3 | 1.6 | 1.7 | 1.2 |
| 20:2 | 0.2 | 0.0 | 0.2 | 0.3 | 0.2 |
| 20:3 | 0.0 | 0.0 | 0.0 | 0.2 | 0.2 |
| 20:4 | 2.1 | 2.0 | 2.0 | 2.2 | 3.1 |
| 20:5 | 6.7 | 6.3 | 9.6 | 10.8 | 17.6 |
| 22:0 | 0.2 | 0.3 | 0.3 | 0.2 | 0.2 |
| 22:1 | 0.6 | 0.9 | 1.8 | 1.1 | 0.6 |
| 21:5 | 0.3 | 0.3 | 0.7 | 0.7 | 0.7 |
| 22:4 | 0.2 | 0.3 | 0.3 | 0.3 | 0.7 |
| 22:5 | 2.6 | 3.5 | 5.0 | 4.0 | 3.5 |
| 22:6 | 26.8 | 40.0 | 43.0 | 44.0 | 36.0 |
| 24:0 | 0.2 | 0.3 | 0.0 | 0.0 | 0.4 |
| 24:1 | 0.6 | 0.7 | 1.0 | 0.8 | 0.7 |

TABLE 10.1-continued

Fatty acid profiles (area %) of oil samples

| Fatty acid | Oil | | | | |
|---|---|---|---|---|---|
| | Tuna oil | Glyceride fraction | Glyceride/FFA20/48 enzymatic re-esterification | Glyceride/FFA24/54 enzymatic re-esterification | Glyceride/FFA55/16 enzymatic re-esterification |
| % Identified | 99.3 | 99.9 | 99.6 | 98.2 | 99.7 |
| % Saturate | 31.3 | 24.6 | 19.2 | 16.7 | 18.1 |
| % Mono-unsaturate | 25.1 | 19.5 | 16.9 | 15.8 | 15.4 |
| % Poly-unsaturate | 42.9 | 55.8 | 63.5 | 65.7 | 66.2 |

TABLE 10.2

Lipid class of oil samples

| Sample | Lipid class (%) | | | |
|---|---|---|---|---|
| | FFA | TG | DG | MG |
| Tuna oil | 0.0 | 100 | 0.0 | 0.0 |
| Glyceride fraction after hydrolysis and distillation | 0.0 | 66.0 | 34.0 | 0.0 |
| After glyceride/FFA20/48 enzymatic re-esterification | 2.5 | 96.1 | 1.1 | 0.0 |
| After glyceride/FFA24/54 enzymatic re-esterification | 0.0 | 99.0 | 1.0 | 0.0 |
| After glyceride/FFA55/16 enzymatic re-esterification | 1.0 | 99.0 | 0.0 | 0.0 |

Example 6

In a sixth example, a refined fish oil (TG17/12 EPA/DHA) was hydrolyzed according to the process described in Example 1 except the *Thermomyces lanuginosus* lipase was used at 0.15% of the oil weight. After hydrolysis and removal of the FFA by molecule distillation, the glyceride fraction (42% yield) was used to react with FFA24/54 and FFA55/16 under the same condition as in Example 3. Fatty acid compositions and lipid class of starting oil, glyceride and FFA fractions of hydrolyzed oil and re-esterified products are shown below in Table 11.

TABLE 11

Lipid class and fatty acid composition of oil samples

| Reaction | Fatty acid composition (area %) | | | | Lipid class (area %) | | | |
|---|---|---|---|---|---|---|---|---|
| | Saturate | Mono | PUFA | EPA/DHA | FFA | TG | DG | MG |
| Refined fish oil | 31.9 | 23.0 | 44.6 | 17.0/12.8 | 0.0 | 100 | 0.0 | 0.0 |
| Glyceride fraction | 27.1 | 17.7 | 55.0 | 14.3/24.3 | 0.0 | 66.4 | 33.3 | 0.3 |
| FFA fraction | 34.7 | 26.4 | 38.8 | 19.0/5.8 | 98.0 | 0.0 | 1.0 | 1.0 |
| After glyceride/FFA24/54 enzymatic re-esterification | 21.1 | 14.3 | 64.6 | 17.1/32.0 | 1.0 | 99.0 | 0.0 | 0.0 |
| After glyceride/FFA55/16 enzymatic re-esterification | 21.4 | 14.0 | 64.4 | 23.9/23.3 | 0.0 | 99.0 | 1.0 | 0.0 |

Fatty acid compositions of FFA20/48, FFA24/54 and FFA55/16 (EPA/DHA) used in the re-esterification reactions are listed in Table 12.

TABLE 12

Fatty acid profiles (area %)

| Fatty acid | Oil | | |
|---|---|---|---|
| | FFA20/48 | FFA24/54 | FFA55/16 |
| 14:0 | 0.2 | 0.2 | 0.7 |
| 16:0 | 0.5 | 0.6 | 1.3 |
| 16:1 | 0.7 | 0.4 | 0.6 |
| 16:2 | 0.1 | 0.0 | 0.6 |
| 18:0 | 0.6 | 1.1 | 0.5 |
| 18:1 | 1.2 | 2.2 | 2.8 |
| 18:2 | 0.1 | 0.2 | 1.0 |
| 18:3 | 0.0 | 0.3 | 0.6 |
| 18:4 | 0.2 | 0.5 | 1.6 |
| 20:0 | 0.4 | 0.3 | 0.0 |
| 20:1 | 2.0 | 2.3 | 0.7 |
| 20:2 | 0.2 | 0.4 | 0.4 |
| 20:3 | 0.2 | 0.4 | 0.7 |
| 20:4 | 2.0 | 2.7 | 6.3 |
| 20:5 | 19.5 | 24.6 | 54.9 |
| 22:0 | 0.6 | 0.0 | 0.0 |
| 22:1 | 7.3 | 1.2 | 0.4 |
| 21:5 | 2.0 | 1.6 | 2.5 |
| 22:2 | 0.0 | 0.0 | 3.4 |
| 22:4 | 0.8 | 0.4 | 0.0 |

TABLE 12-continued

| | Fatty acid profiles (area %) | | |
|---|---|---|---|
| | Oil | | |
| Fatty acid | FFA20/48 | FFA24/54 | FFA55/16 |
| 22:5 | 9.9 | 5.7 | 3.7 |
| 22:6 | 48.7 | 53.7 | 16.8 |
| 24:0 | 0.4 | 0.0 | 0.0 |
| 24:1 | 2.3 | 0.6 | 0.0 |
| % Identified | 99.9 | 99.2 | 99.5 |
| % Saturate | 2.6 | 2.2 | 2.5 |
| % Monounsaturate | 13.5 | 6.3 | 4.5 |
| % Polyunsaturate | 83.8 | 90.6 | 92.5 |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for modifying an oil comprising a glyceride, comprising:
   a) contacting an unmodified oil with a buffer solution of pH 10 and with water;
   b) contacting the unmodified oil with an aqueous solution of *Thermomyces lanuginosus* lipase at a time and temperature sufficient to hydrolyze at least a portion of the glyceride and provide a composition comprising a saturated free fatty acid fraction and a hydrolyzed glyceride fraction;
   c) separating at least a portion of the saturated free fatty acid fraction from the hydrolyzed glyceride fraction; and
   d) esterifying, in the presence of a second lipase, the hydrolyzed glyceride fraction from step c) with a polyunsaturated fatty acid or ethyl ester thereof to produce a modified oil,
   wherein the modified oil comprises greater than 40% omega-3 polyunsaturated fatty acids, 18% to 45% saturated fatty acids, 1% to 15% C18:1 fatty acids, 0% to 10% C16:1 fatty acids, and 60% to 80% of triglycerides, based on the total weight of the modified oil.

2. The method of claim 1, further comprising washing the hydrolyzed glyceride fraction, the saturated free fatty acid fraction, and/or the oil composition with water after step b) and prior to step c).

3. The method of claim 1, wherein the *Thermomyces lanuginosus* lipase is in a phosphate buffered solution of pH 7.2.

4. The method of claim 1, wherein step c) comprises distilling the saturated free fatty acid fraction.

5. The method of claim 1, wherein the *Thermomyces lanuginosus* lipase is 0.0001 to 5% by weight of the total oil composition.

6. The method of claim 1, wherein in step c) the saturated free fatty acid fraction is separated from the hydrolyzed glyceride fraction by a fractionation technique.

7. The method of claim 1, wherein the second lipase comprises *Candida antarctica* lipase B.

8. The method of claim 1, wherein step d) is performed under anhydrous conditions.

9. The method of claim 1, wherein step d) is performed in the absence of organic solvent.

10. The method of claim 1, wherein the weight of the second lipase is 0.1% to 20% total weight of the polyunsaturated fatty acid or ethyl ester thereof, and the hydrolyzed glyceride.

11. The method of claim 1, wherein the polyunsaturated fatty acid or ethyl ester thereof comprises one or more of eicosapentaenoic acid (EPA), docosahexaneoic acid (DHA), or docosapentaenoic acid (DPA).

12. The method of claim 1, wherein the oil composition comprises a microbial oil, plant oil, animal oil, marine oil, algal oil, or combination thereof.

13. The method of claim 1, wherein the oil comprises a crude oil, a semi-refined oil, a refined oil, or a re-esterified oil.

14. The method of claim 1, wherein after step d), the modified oil comprises a higher concentration of polyunsaturated fatty acids than the unmodified oil.

15. The method of claim 1, wherein the modified oil has an EPA/DHA ratio of less than 1:40.

16. The method of claim 6, wherein the fractionation technique is molecular distillation.

* * * * *